(12) United States Patent
Shalaby et al.

(10) Patent No.: US 7,632,765 B2
(45) Date of Patent: Dec. 15, 2009

(54) INORGANIC-ORGANIC MELT-EXTRUDED HYBRID YARNS AND FIBROUS COMPOSITE MEDICAL DEVICES THEREOF

(75) Inventors: Shalaby W Shalaby, Anderson, SC (US); Kenneth W Clinkscales, Easley, SC (US); Kimberly A. Carpenter, Pendleton, SC (US)

(73) Assignee: Poly - Med, Inc., Anderson, SC (US)

( * ) Notice: Subject to any disclaimer, the term of this patent is extended or adjusted under 35 U.S.C. 154(b) by 174 days.

(21) Appl. No.: 11/880,993

(22) Filed: Jul. 25, 2007

(65) Prior Publication Data

US 2008/0183208 A1 Jul. 31, 2008

Related U.S. Application Data

(63) Continuation-in-part of application No. 11/599,691, filed on Nov. 15, 2006, now Pat. No. 7,465,489.

(60) Provisional application No. 60/737,022, filed on Nov. 15, 2005.

(51) Int. Cl.
*D03D 15/00* (2006.01)
*B32B 5/08* (2006.01)
*D04B 21/14* (2006.01)

(52) U.S. Cl. ............... 442/202; 442/199; 442/200; 442/218; 442/308; 442/309; 442/310; 442/311; 428/296.7

(58) Field of Classification Search .......... 442/199, 442/200, 202, 218, 308–311
See application file for complete search history.

(56) References Cited

U.S. PATENT DOCUMENTS

| 4,529,368 | A * | 7/1985 | Makansi ............... 425/72.2 |
| 6,462,169 | B1 | 10/2002 | Shalaby |
| 6,485,749 | B1 * | 11/2002 | Shalaby ............... 424/486 |
| 6,794,485 | B2 | 9/2004 | Shalaby et al. |
| 6,986,859 | B2 * | 1/2006 | Mazany et al. ........ 264/234 |
| 2003/0105256 | A1 * | 6/2003 | Shalaby ............... 526/312 |
| 2005/0277349 | A1 * | 12/2005 | Smith et al. ........... 442/59 |
| 2006/0002979 | A1 * | 1/2006 | Ashammakhi et al. ... 424/426 |
| 2007/0110999 | A1 | 5/2007 | Shalaby |
| 2009/0024151 | A1 * | 1/2009 | Shalaby et al. ........ 606/154 |

* cited by examiner

*Primary Examiner*—Lynda Salvatore
(74) *Attorney, Agent, or Firm*—Leigh P Gregory

(57) ABSTRACT

Composite fibrous constructs are made of combinations of inorganic-organic hybrid monofilament or multifilament yarns containing at least 6 weight percent of inorganic micro-/nanoparticles and organic monofilament or multifilament yarn with typical examples of the hybrid yarn matrix made of absorbable or non-absorbable thermoplastic polymers and final constructs being in the form of knitted or woven meshes and braided ligatures intended to perform under specific mechanically, biologically, and/or radiologically related functions.

6 Claims, No Drawings

INORGANIC-ORGANIC MELT-EXTRUDED HYBRID YARNS AND FIBROUS COMPOSITE MEDICAL DEVICES THEREOF

The present application is a continuation in part of patent application, U.S. Ser. No. 11/599,691, filed on Nov. 15, 2006 now U.S. Pat. No. 7,465,489, which claims the benefit of prior provisional application, U.S. Ser. No. 60/737,022 filed on Nov. 15, 2005.

FIELD OF THE INVENTION

This invention is directed toward the use of inorganic-organic melt-extruded hybrid yarns as part of composite fibrous medical devices which can be used, among other applications, to impart radiopacity to surgical articles and serve as carriers for the controlled release of bioactive agents immobilized onto the inorganic components.

BACKGROUND OF THE INVENTION

Traditional melt-extruded, fine filaments of different cross-sectional geometries having a cross-sectional area at or below 4 mm$^2$ and particularly those having a cross-sectional area of less than 2 mm$^2$ such as monofilament and multifilament yarns used for manufacturing different knitted and woven textile constructs, monofilament sutures, and multifilament braided sutures, are known to be based on thermoplastic crystalline polymers comprising linear chains. An exception to the traditional practice was disclosed by one of the present inventors, wherein polyaxial polymers (with a monocentric branching point) were prepared and converted to strong monofilaments useful for the production of surgical sutures and allied medical products (U.S. Pat. Nos. 6,462,169 and 6,794,485). It is also traditional to incorporate less than 2 weight percent of solid inorganic additives in textile fibers as delustering agents (e.g., TiO$_2$) and to a lesser extent, colorants and heat stabilizers. And frequently, these additives tend to cluster in the polymer melt and interfere with extrusion of articles having small cross-sectional areas as in the case of fiber melt-spinning. In spite of the availability of a great number of inorganic additives that can conceptually impart unique and useful properties to extruded filaments, if used in quantities exceeding 2 weight percent, investigators of the prior art have failed to explore this option to avoid known or perceived complications in the melt-spinning of such inorganic-organic hybrid systems. These facts and contemporary needs for unique hybrid microcomposites in filament form provided a strong incentive to pursue the study subject of the present parent patent application, which is directed to a new family of inorganic-organic hybrid filaments containing at least 10 weight percent of at least one inorganic component uniformly dispersed as microparticles in an organic polymeric matrix to impart one or more useful properties to medical and/or pharmaceutical devices made thereof. And the parent patent application dealt, in general, with a family of inorganic-organic hybrid melt-extruded filaments, which are particularly useful for the production of absorbable/disintegratable coil components of an absorbable/disintegratable endoureteral stent and radiopaque markers or sutures. Clinically novel aspects of incorporating the hybrid filaments in braided or knitted medical constructs, which can, in part, be used for the purpose of imparting radiopacity and/or bioactivity were not disclosed in the parent patent application. Accordingly, these aspects constitute the tenets of the present application.

SUMMARY OF THE INVENTION

This invention is generally directed to a composite fibrous construct having at least one type of inorganic-organic hybrid melt-extruded yarn, the hybrid yarn comprising an organic thermoplastic polymeric matrix component and at least about 6 percent by weight of at least one type of inorganic micro-/nanoparticles dispersed in the polymeric matrix, the hybrid yarn having a structure selected from monofilament yarns and multifilament yarns, and wherein at least some of the inorganic particles are radiopaque to X-ray or radiation used in magnetic resonance imaging.

A specific aspect of the invention deals with a composite fibrous construct as described above, wherein at least one of the bioactive agents is selected from antimicrobial agents, anti-inflammatory agents, anesthetic agents, antineoplastic agents, antiproliferative agents and cell growth promoting agents.

Another specific aspect of this invention deals with a composite fibrous construct comprising at least one type of inorganic-organic hybrid melt-extruded yarn, the hybrid yarn comprising an organic thermoplastic polymeric matrix component and at least about 6 percent by weight of at least one type of inorganic micro-/nanoparticles dispersed in the polymeric matrix, the hybrid yarn having a structure selected from monofilament yarns and multifilament yarns, wherein the inorganic micro-/nanoparticles are selected from the group consisting of oxides, carbonates of multivalent metals, sulfates of multivalent metals, phosphate salts, polymeric phosphate glasses, polymeric phosphate glass ceramics, phosphate ceramics, $ZrO_2$, and basic bismuth carbonate, and wherein the multivalent metals are selected from the group consisting of Mg, Ca, Ba, Sr, Zr, Zn, Bi, and Fe. Meanwhile, the phosphate salts are selected from the group consisting of $CaHPO_4$, $K_2HPO_4$, $KH_2PO_4$, $Na_2HPO_4$, $NaH_2PO_4$, $Ca_3(PO_4)_2$, $Ca_{10}(OH)_2(PO_4)_6$, and $Ca_2P_2O_7$ and the polymeric phosphate glasses are derived from $P_2O_5$, CaO, and at least one oxide selected from the group consisting of ZnO, SrO, $Na_2O$, $K_2O$, $SiO_2$, $Fe_2O_3$, and $ZrO_2$.

A key aspect of this invention deals with a composite fibrous construct comprising at least one type of inorganic-organic hybrid melt-extruded yarn, the hybrid yarn comprising an organic thermoplastic polymeric matrix component and at least about 6 percent by weight of at least one type of inorganic micro-/nanoparticles dispersed in the polymeric matrix, the hybrid yarn having a structure selected from monofilament yarns and multifilament yarns, wherein the organic thermoplastic polymeric matrix comprises an absorbable polyester having chain sequences derived from at least one cyclic monomer selected from the group consisting of ε-caprolactone, glycolide, a lactide, p-dioxanone, 1,5-dioxepan-2-one, trimethylene carbonate, and a morpholinedione, or wherein the organic thermoplastic matrix comprises an absorbable polyether-ester. The absorbable polyether-ester is preferably a polyethylene glycol end-grafted with at least one cyclic monomer selected from the group consisting of ε-caprolactone, glycolide, a lactide, trimethylene carbonate, p-dioxanone, 1,5-dioxepan-2-one and a morpholinedione.

Another key aspect of this invention deals with a composite fibrous construct as described above, wherein the organic thermoplastic polymeric matrix comprises a non-absorbable polymer selected from the group consisting of Nylon 6, Nylon 12, Nylon 11, and a polyalkylene terephthalate.

A technologically important aspect of this invention deals with a composite fibrous construct comprising at least one type of inorganic-organic hybrid melt-extruded yarn, the hybrid yarn comprising an organic thermoplastic polymeric matrix component and at least about 6 percent by weight of at least one type of inorganic micro-/nanoparticles dispersed in the polymeric matrix, wherein the construct is in the form of a braid of the hybrid yarn and at least one other multifilament yarn of an organic thermoplastic polymer, and wherein the braid comprises a core comprising the hybrid yarn and a sheath made of the at least one other multifilament yarn, the hybrid yarn comprising a monofilament. Meanwhile, the inorganic micro-/nanoparticle comprises barium sulfate and the organic thermoplastic polymeric matrix of the hybrid yarn comprises at least one polymer selected from the group consisting of poly-ε-caprolactone, Nylon 6, Nylon 12, and an absorbable segmented polyester derived from one of glycolide and l-lactide and at least one additional cyclic monomer. Additionally, at least one of the multifilament constituent yarns of the braid comprises an organic thermoplastic matrix selected from ultrahigh molecular weight polyethylene, Nylon 6, Nylon 12, Nylon 11, a polyalkylene terephthalate, polypropylene, polyether-ether ketone, and an aromatic polyamide.

A clinically important aspect of this invention deals with a composite fibrous construct comprising at least one type of inorganic-organic hybrid melt-extruded yarn, the hybrid yarn comprising an organic thermoplastic polymeric matrix component and at least about 6 percent by weight of at least one type of inorganic micro-/nanoparticles dispersed in the polymeric matrix, the hybrid yarn having a structure selected from monofilament yarns and multifilament yarns wherein the said construct is in the form of a braid of the hybrid yarn and at least one other multifilament yarn of an organic thermoplastic polymer, and wherein the braid is coated. Furthermore, the coating contains at least one bioactive agent selected from antimicrobial agents, antiviral agents, anesthetic agents, anti-inflammatory agents, antineoplastic agents and cell growth promoting agents.

Another clinically important aspect of this invention deals with a composite fibrous construct comprising at least one type of inorganic-organic hybrid melt-extruded yarn, the hybrid yarn comprising an organic thermoplastic polymeric matrix component and at least about 6 percent by weight of at least one type of inorganic micro-/nanoparticles dispersed in the polymeric matrix, the hybrid yarn having a structure selected from monofilament yarns and multifilament yarns wherein the said construct is in the form of knitted or woven mesh comprising a combination the hybrid yarn and at least one other multifilament yarn of an organic polymer, the hybrid yarn comprising a multifilament yarn, and wherein the mesh is used for hernial repair. Meanwhile, the mesh further comprises a lubricious coating wherein the coating contains at least one bioactive agent selected from antimicrobial agents, antiviral agents, anesthetic agents, anti-inflammatory agents, antineoplastic agents and cell growth promoting agents.

Another aspect of this invention that is of great clinical significance deals with a composite fibrous construct comprising at least one type of inorganic-organic hybrid melt-extruded yarn, the hybrid yarn comprising an organic thermoplastic polymeric matrix component and at least about 6 percent by weight of at least one type of inorganic micro-/nanoparticles dispersed in the polymeric matrix, the hybrid yarn having a structure selected from monofilament yarns and multifilament yarns wherein the said construct is in the form of a high strength suture or ligature for tissue repair.

DETAILED DESCRIPTION OF PREFERRED EMBODIMENTS

The parent patent application provided a clear dispute to the common belief that incorporation of more than about 2 weight percent of inorganic additives for imparting value-added properties to melt-extrudable fiber-forming polymers impairs their conversion into filaments having cross-sectional areas such as those varying between $100\mu^2$ and 4 mm$^2$. In effect, the parent case is directed to hybrid inorganic-organic compositions comprising at least 10 weight percent of an inorganic component present as uniformly dispersed micro-/nanoparticles in absorbable or non-absorbable organic polymeric matrices, which were converted under controlled extrusion conditions to filaments having wide ranges of cross-sectional areas and geometries. The resulting filaments were described as useful components for constructing several forms of medical devices. Recognition of the technological significance of the hybrid inorganic-organic filaments provided an incentive to explore their incorporation in unique composite fibrous constructs targeted for use in specific contemporary medical applications. And this broadened the scope of hybrid filament production to include monofilament and multifilament yarns of traditional dimensions as those used in braided and knitted textile constructs, widely used in the medical industry. Additionally, this invention deals with the formation of continuous hybrid microfilaments for use as radiological markers and filling scaffolds in diseased blood capillaries and vessels in place of currently used metallic microfilaments. Using differently formed constructs containing hybrid microfibers or yarns in radiological applications entails those associated with X-ray and magnetic resonance imaging. A unique application of these radiological markers can be associated with (1) locating and monitoring treated tumor sites; (2) their incorporation in high load-bearing devices, such as in hernial meshes and orthopedic ligatures, for timely detection of mechanical failure of these devices or at the device-tissue interface; (3) monitoring tissue ingrowth, unexpected deformation or dimensional changes at surgical sites or diseased organs; (4) providing guidance during biopsy procedures; and (5) monitoring the physical collapse of absorbable structural devices, which may contain bioactive agents needed during their presence at biological sites. Another aspect of the present invention deals with the use of the inorganic particles in the hybrid filaments as carriers of bioactive agents with specific biological activities depending on the type of sought treatment at the application site. The bioactive agents can be immobilized on the surface of the particles and diffuse outwardly through the absorbable or non-absorbable matrix. It is also possible that as the absorbable filament matrix absorbs, thus releasing the activated particles, the active agents become more bioavailable. Furthermore, part of the agent(s) can be also incorporated in the organic matrix of the hybrid filament to provide more than one release profile of said agent(s). A specific aspect of this invention deals with absorbable or bioactive particles in an absorbable matrix wherein the bioactive particles become available to tissue at the implantation site when the polymeric matrix absorbs. Typical illustrations of this situation are associated with bone or cartilage regeneration and tissue engineering.

Further illustrations of the present invention are provided by the following examples:

EXAMPLE 1

Synthesis of a Segmented Polyaxial Copolyester Glycolide/Caprolactone/Trimethylene Carbonate (G/C/TMC) with 35% $BaSO_4$ by Weight The reaction apparatus comprised a 1L stainless steel kettle with a 3-neck glass lid equipped with an overhead mechanical stirring unit, vacuum adapter, and two nitrogen inlets. An initial charge of 9.1 g. of a polyaxial trimethylene carbonate as polymeric initiator (prepared according to U.S. Pat. No. 6,794,364) and 245 g. of predried barium sulfate was added to the kettle. The initial charge also consisted of 132.1 g. (1.1592 moles) ε-caprolactone, 313.8 g. (2.7048 moles) glycolide. The apparatus was assembled and maintained under reduced pressure at room temperature for at least 20 minutes. The apparatus and its contents were lowered into a high temperature oil bath that was preheated to 40° C.

The system was then purged with nitrogen and the temperature of the oil bath was increased to 95° C. Once the apparatus was purged with nitrogen the vacuum adaptor was removed and a stir bearing was put in its place and stirring at 60 RPM was started. When the monomers appeared melted and well mixed, 2.576 mL of a 0.2M stannous octanoate catalyst solution in toluene ($5.152 \times 10^{-4}$ moles) was added to the kettle. The temperature was increased to 180° C. As the polymerization charge gradually became more viscous, the stirring was slowed proportionally until the charge became too viscous to stir, the stirring was stopped. The reaction was maintained at 180° C. for 7 hours.

The polymer was frozen so that it could be removed and ground. The ground material was transferred to a 2L pear shaped glass flask and placed on a Buchi Rotavapor. After achieving a vacuum of 0.25 mm Hg, the flask was lowered into an oil bath. The temperature was raised to 40° C. After 2 hours at 40° C., the temperature of the oil bath was increased to 80° C. After 1 hour at 80° C., the temperature was increased to 110° C., and maintained at this temperature for 4 hours.

The inherent viscosity, using hexafluoroisopropanol (HFIP) as a solvent and separating the $BaSO_4$, was 1.1 dl/g. The melting temperature and heat of fusion, as determined by differential scanning calorimetry, were 223° C. and 54 J/g, respectively.

EXAMPLE 2

Synthesis of 35-65 by Weight $BaSO_4$—Poly-ε-Caprolactone (PCLB)

A reaction apparatus similar to that described in Example 1 was used for the synthesis of PCLB. Following a procedure similar to that described in Example 1, the initial charge of 0.2708 g. ($3.56 \times 10^{-3}$ moles) of propanediol, 650 g. (5.70175 moles) ε-caprolactone, and 245 g. predried barium sulfate was added to the kettle. The assembled apparatus was placed under reduced pressure and lowered into an oil bath that was preheated to 50° C.

The system was then purged with nitrogen and the oil bath temperature was increased to 120° C. Once the apparatus was purged with nitrogen 2.576 mL of a stannous octanoate catalyst, 0.2M solution in toluene ($5.152 \times 10^{-4}$ moles) was added to the kettle. The vacuum adaptor was removed and a stir bearing was put in its place and stirring at 140 RPM was started. The temperature was maintained at 120° C. for 15 minutes then increased to 160C. As the polymerization charge gradually became more viscous, the stir was slowed proportionally until the polymer became too viscous to stir, the stirring was stopped. The reaction was maintained at 160° C. for 6 hours from the time the stir was stopped.

The polymer was isolated, ground, and dried at 40° C. under reduced pressure. Residual monomer was distilled by heating under reduced pressure until a constant weight is achieved.

The inherent viscosity, using chloroform ($CHCl_3$) as a solvent and filtering the $BaSO_4$, was 1.41 dl/g. The melting temperature and heat of fusion, as determined by differential scanning calorimetry, were 67° C. and 78 J/g, respectively. The molecular weight, $M_n$, $M_w$, and PDI, as determined by GPC using dichloromethane, were 107.7 kDa, 190.2 kDa, and 1.77, respectively.

EXAMPLE 3

Monofilament Fiber Extrusion of MG5B from Example 1

A single screw extruder with four zones was used to extrude the polymer into a monofilament. The polymer was extruded using a 0.6 mm die. A 325 line per inch filter pack was used. Zone 1 was maintained at 100° C. Zone 2 was maintained at 205° C. Zone 3 was maintained at 220° C. Spin Pack was maintained at 225° C. The pump was maintained at 215° C. The metering pump was also operated at 8 rpm while the take up roll was set between 53 and 56 rpm. The collected monofilament had diameters between 0.69 mm and 0.59 mm. The fiber was drawn at 4.1× in the first stage at 60° C. and 0.2× in the second stage at 70° C. resulting in a diameter of 0.36 mm. The resulting fiber had a maximum load of 22.2N, a strength of 31.7 Kpsi, a modulus of 259 Kpsi, and elongation of 26.3%. The free shrinkage was 10.4%.

EXAMPLE 4

Monofilament Fiber Extrusion of PCLB from Example 2

A single screw extruder with four zones is used to extrude the polymer into a monofilament. The polymer is extruded using a 0.6 mm die and a 325 line per inch filter pack. The heat is set as follows for Zones 1, 2, 3, pump, and spin pack, 45° C., 55° C., 60° C., 69° C., and 68° C., respectively, and adjusted accordingly. The metering pump is initially set at 8 rpm and the take up roll will be set to 65 rpm and adjusted to achieve the desired diameter. The collected monofilaments having diameters between 0.8 mm and 0.5 mm are oriented by drawing to a diameter of 0.28-0.38 mm.

EXAMPLE 5

Composite Braid (GB) Construction of Ultrahigh Molecular Weight Polyethylene and Monofilament Yarn of Example 3: General Procedure Initially, ultrahigh molecular weight polyethylene (UHMW-PE) multifilament was plied using a Simet plying unit. The composite braid (GB) constructions required either a single-ply or triple-ply of UHMW-PE multifilament. Next a predetermined amount of UHMW-PE multifilament was wound onto spools using a Herzog SP02 winding unit. These spools were then placed onto either a Herzog RU 2/12-80 or 2/16-80 braiding unit to be used as the sheath of the GB braid.

Meanwhile, the cores of the braids were prepared using either a single-ply or triple-ply monofilament of hybrid monofilament, MG5B. For the single-ply core, the monofilament was wound onto a spool using the Herzog SP02 winder. This spool was then loaded into the appropriate braider by placing it on a tensioning unit located underneath the braider. The monofilament was then fed upwards and joined with the UHMW-PE spools. When a triple ply was used, the monofilament was wound onto three separate spools using the Herzog SP02 winder. These spools were then loaded into a single track on the Herzog RU2/12-80 braider and twisted. Subsequently, the twisted monofilaments were loaded onto the braider using the same method as previously described with the single monofilament core. After braiding, the braid was tightened by threading through an open air heating oven at predetermined through put and tension.

EXAMPLE 6

Construction and Comparative Tensile Properties of Three Composite Braids Made According to Example 5

Braids GB-1a and GB-1b, described in Table I, were constructed using TO 9285-01 Dyneema Purity Low Creep (UG) dtex440 TS60 and a core of single MG5B monofilament. Braid GB-2a was constructed using TO 9285-01 Dyneema Purity Low Creep (UG) dtex440 TS60 and a core of triple-ply MG5B monofilament. Braids GB-3a and GB-3b were constructed using TO 9285-02 Dyneema Purity SGX dtex220 TS80 and a core of triple-ply MG5B monofilament.

TABLE I

Constructions of GB Composite Braids and Their Tensile Properties

| | Construction | | | Tensile Properties | |
|---|---|---|---|---|---|
| Braid # | Sheath | Core | Picks Per Inch | Diameter (mm) | Breaking Strength (N) |
| GB-1a | 12[a] | 1[a] | 51.26 | 1.2 | 560 |
| GB-1b | 12[a] | 1 (3-ply) | 50.11 | 1.3 | 655 |
| GB-2a | 12[a] | 1 (3-ply) | 50.11 | 1.2 | 500 |
| GB-3a | 16 (3-ply) | 1 (3-ply) | 29.79 | 1.8 | 1410 |
| GB-3b | 16 (3-ply) | 1 (3-ply) | 11.02 | 1.6 | 1050 |

[a]Single monofilament

EXAMPLE 7

Synthesis of 35/65 by Weight of Barium Sulfate (BaSO$_4$)/Nylon 6 (N6-B)

A predried stainless steel reactor equipped for mechanical stirring and with inlets for introducing dry nitrogen or applying vacuum is used to prepare N6-B. The reactor is charged with a mixture of □-caprolactam (113 g, 1 mole), 6-aminocaproic acid (1.31 g., 10 mmole) and predried barium sulfate microparticles (61.5 g.). The reactor is purged with dry nitrogen and the polymerization charge is heated under a positive nitrogen atmosphere to about 80° C. to completely melt the caprolactam. The reactants are then heated to 220° C. while stirring to ensure adequate dispersion of the BaSO$_4$ microparticles. Upon reaching 220° C., the stirring is continued until the polymerization charge becomes too viscous to stir (about 4 hours). At this point, the stirring is stopped and the polymerization temperature is raised to 255° C. and the reaction is continued under a positive nitrogen atmosphere for about 20 hours, and subsequently, at 760 mm pressure for an additional 5 hours, and then at 260° C. for 2 hours. To complete the polymerization, the charge is heated at 230° C. for 30 minutes under reduced pressure (~2 mm). The resulting composite system is cooled to room temperature, removed, and ground. The ground product is extracted with water in a Soxhlet extruder for 2 days, dried at 70° C. for 4 hours, and then at 110° C. until a constant weight is achieved.

EXAMPLE 8

Synthesis of 35/65 by Weight of Barium Sulfate (BaSO$_4$)/Nylon 12 (N12-B)

Using a similar method to that used in Example 7, N12-B is prepared (1) using an initial charge of laurolactam (197 g., 1 mole) and 18% aqueous phosphoric acid (12 mL) and BaSO$_4$ (106 g.); (2) heating to about 155° C. to melt the monomer; (3) heating under positive nitrogen pressure according to the following temperature ° C./time (hours) scheme: 160/2, 190/3, 265/20; (4) heating at 760 mm and 260° C. for 2 hours; and (5) heating under reduced pressure (2 mm) and 230° C. for 0.5 hours. The product is isolated and ground. The unreacted monomer is removed by distillation by heating under vacuum. Traces of residual monomer are extracted with 2-propanol. The extracted polymer is dried at 80° C. under vacuum until a constant weight is achieved.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. These subranges are also useful in carrying out the present invention.

What is claimed is:

1. A composite fibrous construct comprising a braid of a hybrid yarn and at least one other multifilament yarn of an organic thermoplastic polymer, the braid comprising a core comprising the hybrid yarn and a sheath made of the at least one other multifilament yarn, the hybrid yarn comprising a monofilament and comprising an inorganic-organic hybrid melt-extruded yarn, the hybrid yarn comprising an organic thermoplastic polymeric matrix component and at least about 6 percent by weight of at least one type of inorganic micro-/nanoparticles dispersed in the polymeric matrix, wherein the inorganic micro-/nanoparticles comprises barium sulfate and the organic thermoplastic polymeric matrix of the hybrid yarn comprises at least one polymer selected from the group consisting of poly-ε-caprolactone, Nylon 6, Nylon 12, and an absorbable segmented polyester derived from one of glycolide and l-lactide and at least one additional cyclic monomer.

2. A composite fibrous construct as set forth in claim 1 wherein the at least one other multifilament yarn comprises an organic thermoplastic matrix selected from ultrahigh molecular weight polyethylene, Nylon 6, Nylon 12, Nylon 11, a polyalkylene terephthalate, polypropylene, polyetherether ketone, and an aromatic polyamide.

3. A composite fibrous construct as set forth in claim 1 wherein the braid is coated.

4. A composite fibrous construct as set forth in claim 3 wherein the coating contains at least one bioactive agent selected from antimicrobial agents, antiviral agents, anesthetic agents, anti-inflammatory agents, antineoplastic agents and cell growth promoting agents.

5. A composite fibrous construct comprising a knitted or woven mesh for hernia repair comprising a hybrid yarn and at least one other multifilament yarn of an organic polymer, the hybrid yarn comprising a multifilament yarn and comprising at least one type of inorganic-organic hybrid melt-extruded yarn, the hybrid yarn comprising an organic thermoplastic polymeric matrix component and at least about 6 percent by weight of at least one type of inorganic micro-/nanoparticles dispersed in the polymeric matrix, the hybrid yarn having a structure selected from monofilament yarns and multifilament yarns, the mesh further comprising a lubricious coating.

6. A composite fibrous construct as set forth in claim 5 wherein the coating contains at least one bioactive agent selected from antimicrobial agents, antiviral agents, anesthetic agents, anti-inflammatory agents, antineoplastic agents and cell growth promoting agents.

* * * * *